United States Patent [19]

Bosscher

[11] 4,024,499
[45] May 17, 1977

[54] AUDIOMETRIC SYSTEM

[75] Inventor: Jack F. Bosscher, Lake Worth, Fla.

[73] Assignee: Oto-Data, Inc., Atlanta, Ga.

[22] Filed: June 24, 1974

[21] Appl. No.: 482,002

[52] U.S. Cl. .............................. 340/146.2; 179/1 N; 340/146.1 BA; 340/172.5
[51] Int. Cl.² .......................................... H04M 1/00
[58] Field of Search ............... 340/172.5, 146.1 D, 340/146.1 BA, 146.2; 179/1 N; 235/153, 177, 61.7 A

[56] References Cited

UNITED STATES PATENTS

| 2,242,196 | 5/1941 | Thompson et al. | 340/146.1 BA |
| 3,562,708 | 2/1971 | Verbarg et al. | 340/146.1 R |
| 3,582,880 | 6/1971 | Beausoleil et al. | 235/153 AH |
| 3,651,484 | 3/1972 | Smeallie | 340/172.5 |
| 3,753,243 | 8/1973 | Ricketts, Jr. et al. | 340/172.5 |
| 3,784,980 | 1/1974 | Geesen | 340/146.2 |
| 3,794,981 | 2/1974 | O'Connor | 340/146.2 |
| 3,809,811 | 5/1974 | Delisle et al. | 179/1 N |
| 3,846,626 | 11/1974 | Yoshida | 235/177 |

Primary Examiner—Malcolm A. Morrison
Assistant Examiner—Errol A. Krass

[57] ABSTRACT

Audiometric system for monitoring manually-conducted hearing tests and for automatically recording the results of such tests. The system includes a modified audiometer for applying tones to a subject at selected frequencies and amplitudes, and a data interface for converting the control settings of the audiometer to digital data in a format suitable for operating printing apparatus to make a printed record of the audiometric test data in predetermined format. The digital data may also be recorded for subsequent analysis or other use. The data interface provides various operational safeguards which assist the audiometer operator in the desired performance of the audiometric testing procedure.

17 Claims, 4 Drawing Figures

AUDIOMETRIC SYSTEM

INTRODUCTION

This invention relates in general to audiometric systems and in particular to an audiometric system including a data interforce subsystem which is particularly useful for administering and recording audiometric tests.

Audiometric testing to determine a person's hearing capability is a well-known technique, consisting generally of selectively exposing the subject to audio tones of selected frequencies and amplitudes. The results of an audiometric test provide a hearing profile for the subject, so that he can know whether his hearing is "normal" within accepted limits.

Although audiometric testing of hearing ability has been known and used for some time, recently enacted legislation has emphasized the need to provide periodic hearing tests for persons whose work environment subjects them to certain levels of noise. Workers in occupations such as airline ramp attendants and factory workers, for example, are frequently exposed to high levels of noise which may cause permanent impairment of hearing unless suitable protective equipment is provided, either to suppress the noise at its source or to protect the ears of the workers. Moreover, some types of equipment provide audible alarms or signals which might go unheeded by persons having impaired hearing, with possible injury to persons or property. For these reasons, it has become even more important to provide audiometric testing of large numbers of individuals on a periodic basis, so that any long-term changes in the hearing characteristics of an individual can be detected.

Audiometric equipment of the prior art consists generally of apparatus for generating tones of variable frequency and amplitude, at the control of an operator who makes manual entries on a sheet of paper in response to the test subject's observed ability or inability to hear a tone. When it is considered that a typical audiometric test consists of tones of several separate frequencies, with each frequency tone applied at 5-decibel (db) levels commencing at 110 db, for example, and decreasing to the threshold of audibility for a particular subject, it will be understood that manual administration of audiometric test is time-consuming and subject to error in the manual notation of test results. The manual administration of audiometric tests for large numbers of employees on a periodic repetitive basis would be even more expensive and burdensome.

While automated audiometric equipment has been proposed, such equipment generally attempts to combine the basic features of a standard audiometer with additional functions such as hearing pattern recognition, automatic pretest, automatic threshold determination, and a number of other factors which, while worthwhile for some clinical purposes, are generally not required for administering basic audiometric tests. Moreover, such automatic equipment of the prior art is generally incorporated into a basic audiometer, so that the purchase of the equipment becomes substantially more expensive than the purchase of an equal number of basic audiometers.

THE INVENTION

Accordingly, it is an object of the present invention to provide an improved audiometric system.

It is another object of the present invention to provide an improved audiometric system for automatic recording of test results.

It is still another object of the present invention to provide an audiometric system which converts the control settings of an audiometer to data in form for printing or otherwise recording the results of an audiometric test.

It is still another object of the present invention to provide an audiometric system in which deviations of the operator from a predetermined test sequence cannot be incorrectly recorded.

Other objects and advantages of the present invention will become apparent from the following description of the disclosed embodiment, in which:

Stated in general terms, the present invention provides an audiometric system in which the control settings of an audiometer are converted to digital data which is then converted to a form appropriate for operating printing apparatus or for application to data processing equipment. The present system preferably includes circuitry for remembering the previous setting of an audiometer control, for comparing the previous control setting with a present control setting as verification that the audiometer control settings are being selected in a predetermined test sequence, and for providing proper printer operation if the sequence is changed. The present system prevents the audiometer operator from inadvertently making more than one test at the same setting of the audiometer controls. The present audiometric system in preferred form is conveniently adaptable as an interface for connection between a modified conventional audiometer and a conventional printer such as a teletype machine.

Figure 1:
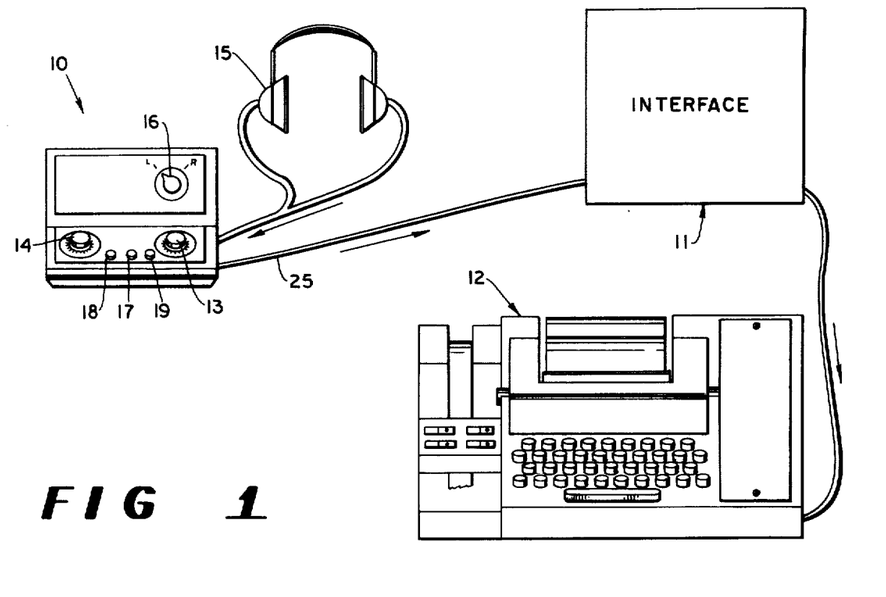
FIG. 1 shows a general block diagram of the disclosed embodiment.

Stated more specifically and with reference to the disclosed embodiment of the invention, there is shown in FIG. 1 an audiometric system including an audiometer 10, an interface 11, and a suitable data utilization device such as the printer 12. The audiometer 10 may be any audiometric instrument which is operable to provide tone signals of selectively adjustable frequency and amplitude, in the manner known to those skilled in the art. The present invention is particularly adaptable for use in combination with an audiometer 10 which can be provided by conventional commercially available audiometers with relatively uncomplicated modifications as described, however, and an actual embodiment of the present invention uses a Beltone Model 9-D audiometer modified to provide output signal conditions indicating the positional settings of certain audiometer controls.

The operating controls of the typical audiometer generally include a frequency selector 13, which selects the tone frequency, and an attenuator control 14, which adjusts the amplitude of the selected frequency tone in five-decibel (db) steps commencing at a predetermined level such as, for example, 110 db. Those skilled in the art will recognize that the term "decibel" denotes magnitude relative to a predetermined reference level. The tone signals of selected frequency and amplitude are applied to the earphones 15, which are worn by the person being tested. A left-right ear switch 16 is provided on the audiometer, so that the tone can be applied only to a selected ear of the test subject, inasmuch as the hearing characteristics of each ear must be independently tested.

The tone switch 17 is actuated by the operator to apply the selected tone signal to the earphones 15. The audiometer 10 also includes the record control 18 and the reset control 19, which control operations of the present system as described hereinbelow.

Since the basic audiometric test data to be recorded is determined by the settings of the frequency selector 13, the attenuator 14, and the left-right switch 16, it is necessary to convert the positions of these controls to electrical signals which uniquely correspond to the switch positions. Since the attenuator 14 of a typical audiometer is settable in five-db increments ranging from zero to 110 db, the disclosed embodiment of the invention uses a code disc which is attached within the audiometer 10 to the control shaft of the attenuator 14. The code disc encodes the rotary position of the attenuator shaft, using five-bit binary code in a manner known to those skilled in the art. The binary characters on the code disc may be provided by perforations in the disc, in combination with photosensitive devices and illumination sources such as lightemitting diodes or the like. Alternatively, the code disc can be constructed using electrically conductive binary bits in combination with suitable brushes or other contact devices. The code disc is not depicted herein, inasmuch as the design and construction of code discs for converting rotary shaft angular position information to multiple-bit binary data is known to those skilled in the art.

The five-bit binary information corresponding to the position of the attenuator 14 is supplied along the conductors collectively identified at 23 to the D-register 24 (FIG. 2), contained within the interface 11. It is understood that the conductors 23, along with other conductors extending from the audiometer 10 to the interface 11, form a portion of the interconnecting cable 25 extending from the audiometer to the interface.

Figure 2:
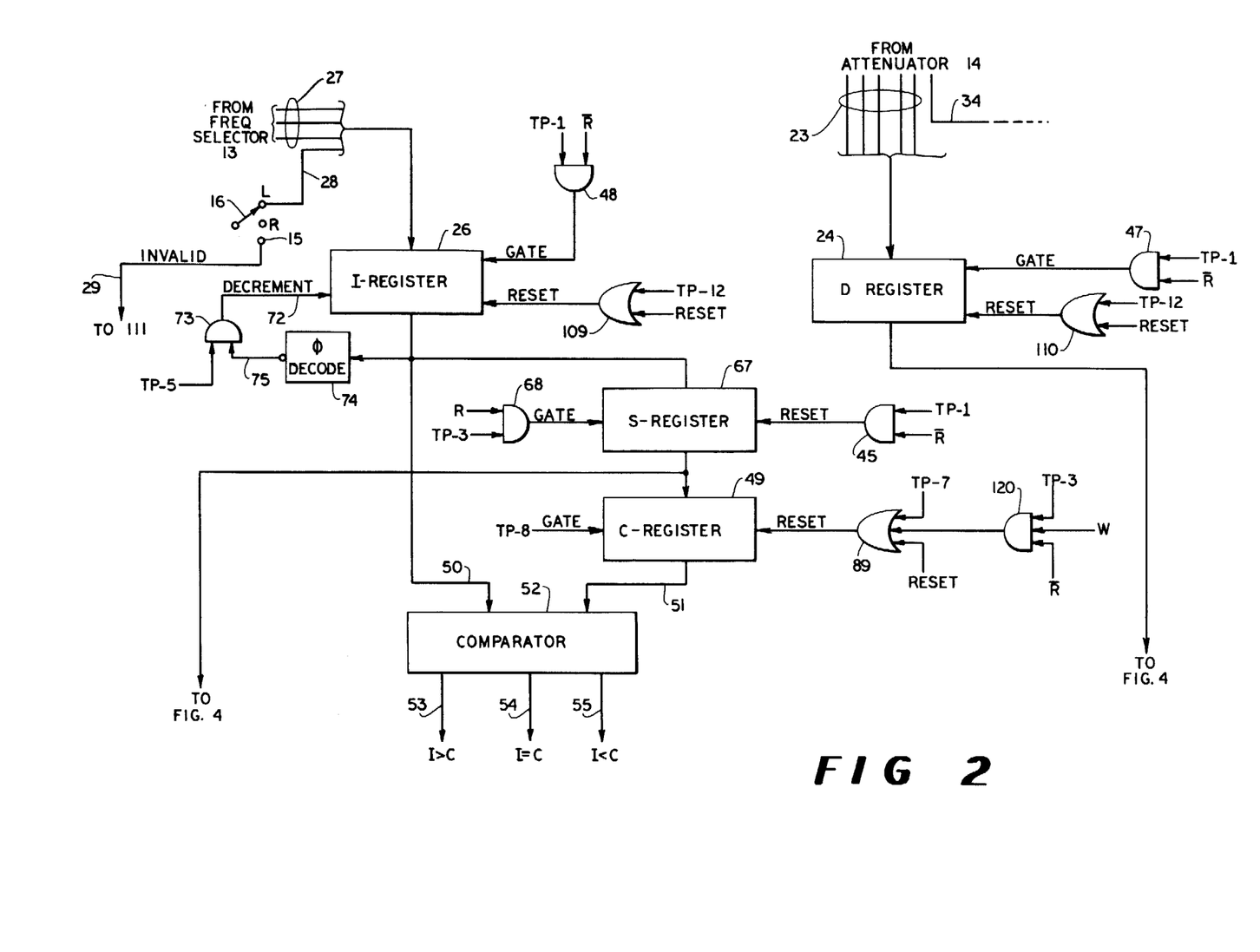
FIG. 2 shows a block diagram of the data storage register arrangement for the interface apparatus of the disclosed embodiment.

The rotary position of the frequency selector 13 can also be provided to the interface by a separate digital encoding disc connected to the shaft of the frequency selector, if desired. Alternatively, however, digital signals corresponding to desired positions of the frequency selector can be provided by simply providing an additional switch gang on the rotary frequency selector, since the number of frequency selector positions of interest is typically sufficiently small to enable a 3-bit binary signal to suffice. The 3-bit signal corresponding to frequency selector position is supplied to the I-register 26 of the interface along the conductors collectively designated 27.

An additional data bit is supplied to the I-register 26 along the line 28 connected to the ear switch 16. Since only two positions of the ear switch 16 are of interest, in the disclosed embodiment of the present invention, one of the two possible ear switch positions, such as "left ear", can be connected to the I-register so that the presence of a logic "one" signal on the line 28 corresponds to selection of the left ear by the switch 16 and the absence of the aforementioned logic signal on the line 28 denotes the selection of the right ear.

Since the disclosed embodiment of the present system is specifically designed for use with a modified conventional audiometer 10, the control switches of the audiometer may include setting positions which are not used in the testing operations for which the present invention is provided. It is desirable, therefore, to provide the present invention with some means for detecting when an unused or "invalid" position of an audiometer control switch has been inadvertently selected by the operator of the audiometer, so that the operation of the system can be inhibited while the invalid switch position is maintained. The ear switch 16, for example, has a third position 16' which is not used, in the disclosed embodiment, and which is connected to the interface 10 through the line 29 for a purpose described below. Other controls of the audiometer 10, such as the frequency selector 13, may have control positions which can be designated as "invalid" positions, providing that the encoding means associated with the switch provides an "invalid" binary state corresponding to the designated invalidity.

Figure 3:
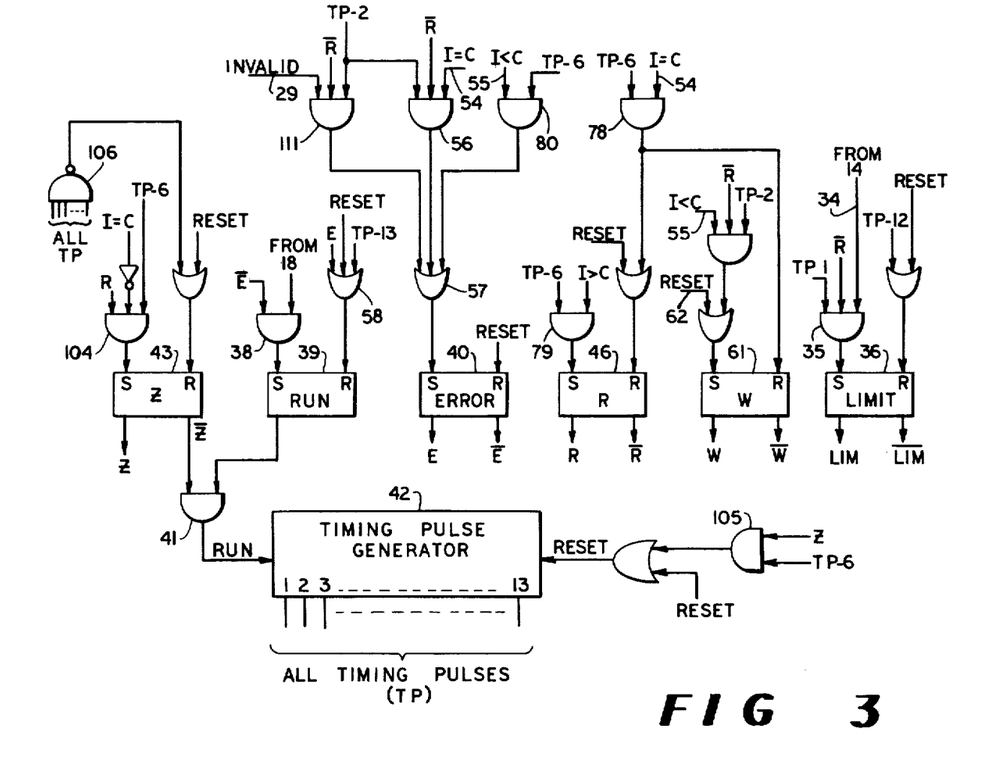
FIG. 3 shows a block diagram of the operational control logic for the interface apparatus of the disclosed embodiment.
Figure 4:
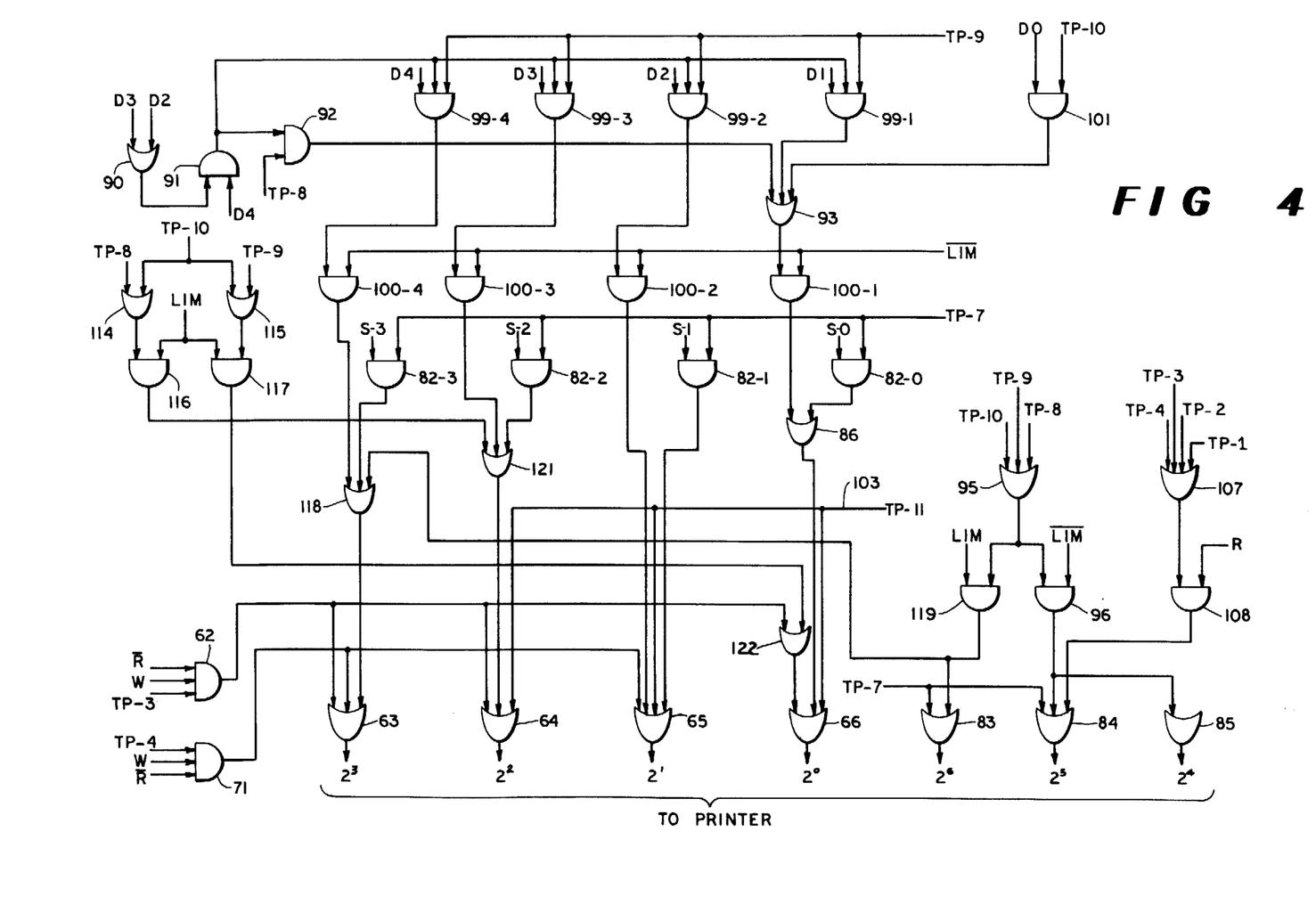
FIG. 4 shows a block diagram of the binary output coding logic for the interface apparatus of the disclosed embodiment.

Turning to the disclosed embodiment of the interface 11, the interface includes a number of data registers which are shown in FIG. 2, a number of control flip-flops and other logic elements, and a source of timing pulses, shown in FIG. 3; and circuits shown in FIG. 4 for converting the control setting data input signals to machine-readable logic output signals suitable for conversion to ASCII printer code or for other applications. The division of the interface among the various drawing figures is only for descriptive purposes, however, and is not intended to imply a corresponding division of the interface per se.

In the disclosed embodiment, it is desired that the maximum available setting of the attenuator 14 (110 db, with the exemplary audiometer 10) be indicated by printing the characters "lim", indicating the upper-limit setting of the attenuator, rather than printing the actual corresponding numerals. The limit setting of the attenuator control is identified by a logic signal generated at the attenuator code disc and applied along the line 34 to the AND gate 35 associated with the set input of the limit flip-flop 36. A logic 1 is present on the line 34 only when the attenuator 14 is in the upper-limit setting, whereupon the code disc concurrently applies logic zero signals to all inputs of the D-register 24.

The data recording operational sequences of the interface 11, described in detail below, are initiated in response to operator actuation of the record control 18 located on the audiometer 10. Operation of the record control 18 applies a logic signal on the line 37 which, as seen in FIG. 3, is connected to the AND gate 38 associated with the set input of the run flip-flop 39. The run flip-flop 39 is set by actuation of the record control 18, assuming the error flip-flop 40 is presently reset, causing a logic signal to be applied through the AND gate 41 to initiate operation of the timing pulse generator 42. It is assumed at this time that the Z flip-flop 43 is reset. The timing pulse generator, in response to the start signal, commences producing a sequence of thirteen separate timing pulses with the timing pulses occurring at ten-millisecond intervals and with no overlap between timing pulses. Each operational phase of the interface is controlled by the timing pulses in a manner described below.

At time TP1, assuming that the R flip-flop 46 is not set, the D-register 24 and the I-register 26 are each gated to receive a logic signal corresponding to the respective audiometer control setting inputs on the lines 23 and 27. The D-register is gated by the application of TP1 to the AND gate 47, and the I-register is gated in a similar manner by the application of TP1 to the AND gate 48. One of the logic inputs applied to the I-register, it will be recalled, is a signal indicating the position of the left-right switch 16. All of the necessary control setting data from the audiometer 10 is received and stored in the interface 11 at TP1, accordingly, with the assumption that the R flip-flop is not set. The S-register 67 is reset to zero by the application of TP1 to the AND gate 45, assuming that the R flip-flop 46 is reset.

Following the foregoing step of data storage in the D and I-registers, the contents of the I-register are compared with the contents of the C register 49 remaining from a previous recording step. It is assumed for the purpose of the present explanation that the instant recording step is the first such step in a series, and that the C-register 49 was previously reset to a logic zero state. The manner in which the C-register becomes set and reset is described below.

The logic contents of the I-register 26 and of the C-register 49 are applied along respective lines indicated at 50 and at 51 to the comparator 52. The comparator 52 provides a logic output signal on one of the three outputs 53, 54, and 55, respectively depending on whether the number stored in the I-register is greater than that of the C-register, is equal to that of the C-register, or is less than that of the C-register. Since the frequency selector 13 is assumed to be initially set at a position arbitrarily designated "position one", corresponding to the first position on a pre-printed form which can be used in the printer 12, and since the C-register is initially at a logic state corresponding to zero, the comparison of the I-register and the C-register provides an output along the line 53 indicating that I is greater than C. If I is equal to C, which is more likely to occur in subsequent recording steps as indicated below, the signal on the line 54 is applied to the AND gate 56 (FIG. 3) and, at time TP2, a signal is applied through the OR gate 57 to set the error flip-flop 40. Setting the error flip-flop 40 applies the error set signal to the OR gate 58 to reset the RUN flip-flop 39, whereupon the operation of the timing pulse generator 42 is interrupted and the remainder of the data recording operation is suspended.

Since the present recording step is assumed to be the first in a series of steps, it is necessary that the printer 12, which may be provided by a conventional apparatus such as a Model 33 ASR teletype, receive a carriage return signal to properly position the printer for the subsequent data printing steps. The carriage return signal is generated at time TP3, assuming that the R flip-flop 39 is reset and the W flip-flop was set in response to a reset signal on the line 62 from the reset control 19 by the audiometer operator at the begining of the first data recording operation. Referring to FIG. 4, it is seen that the AND gate 62 applies a signal at TP3 to each of the OR gates 63, 64 and 66, the outputs of which are designated respectively as $2^3$, $2^2$, and $2^0$. The output signals from the aforementioned three OR gates provide a standard ASCII carriage return signal in binary code.

Als at TP3, the data stored in the I register 26 is gated to the S register 67 in response to a gating signal from the AND gate 68. At this time, accordingly, the I-register and the S-register each contains identical data corresponding to the settings of the frequency selector 13 and the left-right switch 16.

At time TP4, because the W flip-flop 61 is set and the R flip-flop 46 is presently reset, a signal from the AND gate 71 (FIG. 4) is applied to the OR gates 63 and 65 to generate an ASCII "line feed" character for use by the printer 12.

The I-register 26 is a register which can be selectively decremented by one, in response to a downcount signal applied to the input 72. Such input is applied in response to the occurrence of TP5 at the AND gate 73, unless a logic zero condition is present in the I-register as determined by the decoder 74. The decoder 74 can simply be a AND gate connected to each of the binary output lines of the I-register 26, so that the line 75 provides a logic "one" to the AND gate 73 indicating 0 only when all outputs of the I-register are at logic "zero". For all data recording operations other that the first such operation, it will be seen that the count in the I-register is now less than the count in the S-register by one.

Turning next to the events occurring at timing pulse TP6, the I-register is again compared with the C-register. Since the I-register initially contained a count of one and was downcounted to zero, and since the C-register 49 was initially set to a count of zero, the I=C output on the line 54 is applied to the AND gate 78 (FIG. 3) to reset the W flip-flop 61 at TP6. The R flip-flop 45, if previously set, is also reset at this time in response to I=C.

If the contents of I-register remained greater than the contents of the C register at TP6, the output on the line 53 of the comparator 52 would be applied to the AND gate 79 (FIG. 3) to set the R flip-flop 46. The purpose and result of setting the R flip-flop in response to I greater than C is explained below.

If I is less then C at time TP6, an error condition exists and the signal on the line 55 of the comparator 52 is applied to the AND gate 80 (FIG. 3) to set the error flip-flop 40; the run flip-flop 39 is thereby reset, terminating further operation of the data recording step.

Assuming that I=C at TP6, the interface operation next moves to events occurring in response to timing pulse TP7. The contents of the S-register 67, which correspond to the original contents of the I-register, are gated at TP7 to the data conversion logic shown on FIG. 4. Turning to FIG. 4, the four-bit ouput from the S register is designated S0, S1, S2, S3, and each bit is applied through respective AND gates 82-0, 82-1, 82-2, and 82-3, in response to TP7, and the OR gates 86, 117, and 118 to gate the binary logic of the S-register to the lower four bits of the data conversion circuitry shown in FIG. 4. The TP7 input is also applied to the OR gates 83 and 84, corresponding to the $2^6$ and $2^5$ print code bits, which those skilled in the art will recognize as controlling lower-case operation of the printer. Those skilled in the art will also recognize that the data bits present in the outputs $2^0$–$2^6$ are provided in parallel form, and must undergo appropriate parallel-to-serial conversion in conformance with conventional EIA interface standards. Such parallel-to-serial conversion is well within the abilities of those skilled in the art and may be accomplished, for example, with the use of a conversion chip such as the Motorola chip MC 2257L.

Accordingly, the frequency data and the ear data are supplied at TP7 in the form of lower-case ASCII character signals which can be used to operate the printer 12, or which can be recorded on any suitable medium such as magnetic tape, perforated tape, or the like for subsequent use. The C-register 49 is now reset to zero in response to TP7 acting though the OR gate 89, thereby preparing the C-register for the following operational step. The C-register is initially at a zero state, it will be recalled, for the first data recording operation.

At TP8 the C-register is gated to receive the contents previously stored in the S-register 67. The C-register now contains the contents that were originally stored in the I register at TP1 of the particular data recording operation.

The timing pulse TP8 also controls gating of the first character from the D-register to the printer interface. If the D-register contains a signal corresponding to an attenuator setting of 100 db or greater, then the character 1 must be printed at this time. The binary output signals D2 and D3 from the D-register are applied to the OR gate 90 (FIG 4), while the output D4 is applied to the AND gate 91. A D-register state corresponding to an attenuator setting of at least 100, accordingly, provides a logic signal to the AND gate 92 which, at TP8, provides an input signal through the OR gate 93, the AND gate 100-1 (assuming the limit flip-flop 36 is presently reset), and the OR gate 86 to drive the $2^0$ binary bit. The timing pulse TP8 is also applied through the OR gate 95 and the AND gate 96, assuming the limit flip-flop is reset, to provide a mandatory output signal on the $2^4$ and $2^5$ bits, whereupon is provided the ASCII code for printing the numeral 1. It will be understood that the D-register contains a logic signal indicating a "first character" at all times, since a first character of zero is printed for attenuator settings less than 100.

The second character of the information stored in the D-register is printed at TP9. The four binary bits D1–D4 from the D-register are respectively connected to the AND gates 99-1, 99-2, 99-3, and 99-4. The binary signals applied to the AND gates 99 are gated, at TP9, to a second group of AND gates 100-1 through 100-4, and, in the presence of a reset signal from the limit flip-flop 36, provide corresponding logic outputs at the $2^0$ through $2^3$ printing interface lines. The TP9 pulse is also applied to the OR gate 95 to force the $2^4$ and $2^5$ bits, thereby providing an ASCII output signal corresponding to the second character of the attenuator setting indicated by the binary information contained in the D-register.

The third and last character corresponding to data in the D-register is provided to the printer interface at TP10. Since the attenuator 14 of the audiometer used in the disclosed embodiment is calibrated in five-db increments, the third digit is either a 0 or a 5. The low-order binary bit D0, from the D-register, is used in the disclosed embodiment to denote the numeral 5 if true, and to denote the numeral 0 if false. The binary bit D0 is gated through the AND gate 101 at TP10, through the OR gate 93, and the AND gate 100-1 if the limit flip-flop 36 is reset, to control the $2^0$ output bit. The $2^4$ and $2^5$ bits are also forced at TP10, and so the ASCII code corresponding either to a 5 or a 0 is provided in response to the logic condition of the D-register output D0.

It will be recalled that the maximum available setting of the attenuator 14, in the disclosed embodiment, causes the limit flip-flop 36 to be set and also causes the D-register to receive a logic zero input. The absence of the limit reset signal at times TP8, TP9, and TP10, along with the logic-zero output signals from the D-register, prevent the character printing operations described in the preceding paragraphs from occurring. In the alternative, where the limit flip-flop 36 was previously set at TP1, the $2^0$, $2^2$, $2^3$, and $2^6$ bits are controlled at TP8, TP9, amd TP10 through signals provided by the OR gates 114 and 115, and the AND gates 116, 117, and 119, so that the printer is supplied with the appropriate binary coded information necessary to print the characters "lim" at TP8, TP9, and TP10. The logic signals are applied to the $2^0$, $2^2$, $2^3$ OR gates 66, 64, and 63 through the respective OR gates 122, 121, and 118.

It will now be seen that all of the switch position data previously received from the audiometer 10 and stored in the interface 11 has been provided as output from the interface to the printer 12 (or, alternatively to a suitable data recording apparatus), and the end of the data delivery from the interface 11 is positively signalled by providing an ASCII 07 control character in response to application of TP11 on the line 103.

The I-register 26 and the D-register 24 are both reset to zero in response to application of the TP12 pulse through the OR gates 109 and 110 to the respective registers. The I-register and the D-register are now conditioned to receive audiometer switch setting information in response to TP1 of a subsequent data recording operation. It will be recalled that the S-register 67 was previously reset at TP1, and that the C-register 49 presently contains the information initially loaded into the I-register at the beginning of the present recording operation. The run flip-flop 39 is reset by application of timing pulse TP13 through the OR gate 58, stopping operation of the timing pulse generator 42 and terminating the particular data transfer operation. The apparatus is now ready for a subsequent data transfer operation in response to operation of the record control switch 18 on the audiometer 10.

Although the administration of an audiogram normally progresses with the frequency selector 13 being incremented to provide an ascending progression of frequency tones, an operator may desire to return the frequency selector 13 from a previous frequency setting to a lower-frequency setting. The fact of any such return must be provided to the printer 12, so that the data associated with the returned-frequency operation is not erroneously printed out in a location normally reserved for the next-higher sequential frequency. Assuming that a data recording operation is initiated by operating the record control 18 after the frequency selector 13 has been returned to a lower frequency, the comparison of the registers I and C at TP2 provides a signal on the line 55, indicating that the contents of the C-register is greater than that of the I-register, and the W flip-flop 61 becomes set at this time (assuming that the R flip-flop 46 is reset). A "carriage return" signal is subsequently provided to the printer at TP3, and a line "feed" is provided at TP4.

For example, assume that the operator of the audiometer 10 has backed up the frequency selector 13 from position 5 to position 4. Since the data for each position of the frequency selector is assumed to be printed at predetermined columns by the printer 12, and since a printer received a "carriage return" input at TP3 in response to the backward movement of the frequency selector, it will be understood that the printer must receive four sets of "space" signals to properly position the printer for printing the data now stored in the I-register and corresponding to position 4 of the frequency selector 13. The necessary spacing steps are accomplished in the following manner. The I-register is decremented by one at TP5, and the contents of the I and C registers are again compared at TP6. Since the I-register now contains a count of 3 and the C-register contains a count of 0, I is greater than C and the R flip-flop 46 becomes set, indicating that at least one additional "space" output must be supplied to the printer. (The C-register was previously reset to zero at TP3, in response to the W flip-flop set signal applied through the AND gate 120). The set signal from the R flip-flop 46 is applied to the AND gate 104 connected to the set input of the Z flip-flop 43; the Z flip-flop also becomes set at TP6, accordingly, in the absence of an I=C condition. Setting of the Z flip-flop 43 removes an input from the AND gate 41, interrupting operation of the timing pulse generator 42 at TP6. The reset signal from the Z flip-flop is applied at this time to the AND gate 105, whereupon the inoperative timing pulse generator is now reset to zero. The zero state of the timing pulse generator applied to the AND gate 106, resets the Z flip-flop 43 and allows the timing pulse generator 42 to commence delivering a new train of timing pulses.

Since both the R and W flip-flops remain set, the I-register and D-register cannot receive new switch setting information at this time, however. Referring now to FIG. 4, each of TP1, TP2, TP3, and TP4 is applied through the OR gate 107 and, since the R flip-flop is set, through the AND gate 108 to the OR gate 84 associated with the $2^5$ bit, which corresponds to the signal for an ASCII "space". Each of the aforementioned four timing pulses generates a "space" signal to the printer. The absence of the R flip-flop reset signal on the AND gates 62 and 71 prevents a "carriage return" or "line feed" from occurring at this time.

The contents of the I-register is again decremented by one at TP5, and then compared with the contents of the C-register at TP6. If I is still greater than C, the R flip-flop remains set, the Z flip-flop 43 is set, and the foregoing sequence of reset events is repeated to generate another set of four "space" signals to the printer. It will be seen, accordingly, that the foregoing spacing sequence repeats itself, causing a set of four "space" signals to be generated for each repeat operation, until the I-register has been decremented to equal the C-register. At this time, the printer has been supplied with signals to forward-space the proper number of spaces to print the data corresponding to position 4 of the frequency selector 13.

Although the disclosed system allows the audiometer operator to record data after changing the frequency selector position in either direction, i.e., incrementally or decrementally, the system will not respond to a situation where no change in the setting of the frequency selector has been made since the last data recording operation. A no-change situation could occur, for example, where the audiometer operator inadvertently fails to select another frequency, after completing a particular portion of a test. The absence of any change in the setting of the frequency selector 13 is detected at TP2, in response to an output signal on line 54 of the comparator 52 corresponding to the switch setting signals on the I-register and the C-register. An I=C signal at TP2 is applied to the AND gate 56 and, assuming the R flip-flop 46 is reset, causes the error flip-flop 40 to be set. Setting of the error flip-flop 40 resets the run flip-flop 39, terminating operation of the timing pulse generator 42. The data transfer operation is interrupted at this point, and a suitable audible and/or visible signal can be provided to advise the operator that an error condition exists. The operator can overcome the error condition by selecting an appropriate setting of the frequency selector 13 and then operating the reset control 19 to reset the error flip-flop 40 and the timing pulse generator 42, after which the data transfer operation is again intiated in response to operation of the record control 18.

The error flip-flop 40 also becomes set in response to application of an invalid switch position signal to the AND gate 111. An invalid signal can be provided from the switches associated with any or all of the frequency selector, the attenuator, and the left-right switch, for example, corresponding to a switch position which is inconsistent with audiometric tests applied with the present system. The error condition is reset as aforementioned by initially correcting the switch setting which caused the invalid signal and by then operating the reset control 19.

The error flip-flop 40 is also set, if the contents of the C-register is somehow greater than the contents of the I-register at TP6, through the AND gate 80 associated with the set input of the error flip-flop 40.

It will be obvious that the foregoing relates only to a preferred embodiment of the present invention, and that numerous alterations and modifications may be made therein without departing from the spirit and the scope of the invention as defined in the following claims.

What is claimed is:

1. Audiometric data conversion apparatus for converting audiometer switch position settings to printable output data, comprising:
   first circuit means connected to receive a present input signal condition corresponding to a present position of a first selectively variable input switch means;
   second circuit means operative to retain a prior input signal condition corresponding to a prior position of said first switch means, said second circuit means being selectively operative to receive such prior input signal condition previously received in said first circuit means;
   comparison means responsive to said present input signal condition retained in said first circuit means and to said prior input signal condition in said second circuit means, said comparison means being operative to provide an output signal condition corresponding to a relation between the prior and the present positions of the switch means;
   third circuit means selectively operative to receive the present input signal condition only in response to a predetermined ouput signal condition from said comparison means indicating that a certain said relation exists between said present and prior switch positions; and
   sequential control means initially operative in response to a control signal condition which is independent of said input signal conditions to operate said third circuit means, and subsequently operative to transfer said present input signal condition to said second circuit means in substitution of said prior input signal condition previously retained therein.

2. Apparatus as in claim 1, further comprising:
   error circuit means responsive to a signal condition from said comparison means corresponding to identity of the prior and present switch positions to provide an error signal condition; and means responsive to the occurrence of said error signal condition to render said third circuit means inoperative.

3. Apparatus as in claim 2, further comprising reset circuit means responsive to the coincident occurrence of a reset input signal and the absence of said error signal condition to render said third circuit means operable.

4. Method of converting manually determined plural positions of an audiometer control switch to data output signals; comprising the steps of:
determining a first input signal corresponding to a first certain position of the switch;
storing said first input signal;
determining a second input signal corresponding to a second certain position of the switch;
comparing said first and second input signals to determine the possible change between the first and second positions of the switch;
providing an output signal condition corresponding to said second position only when a certain predetermined change in said first and second positions of said switch is determined by said comparison; and
providing an error signal condition when said first and second positions of the switch are identical.

5. Method as in claim 4, wherein:
said output signal condition comprises binary coded digit information corresponding to said second position of the switch, and is provided only when said comparison determines that a certain predetermined change exists between said first and second positions of said switch.

6. Method as in claim 4, further comprising the steps of:
determining a input signal corresponding to the setting position of a second switch; and
after said output signal condition occurs, providing a second switch output signal condition corresponding to said setting position of said second switch.

7. Method as in claim 6, wherein said second switch output signal condition is provided in binary coded digit information corresponding to said independent input signal.

8. Method as in claim 7, wherein:
said independent input signal includes a limit signal component when said second switch is at a certain setting; and
said second switch output signal condition corresponds to a predetermined group of certain indicia in response to said limit signal component.

9. Method of converting manually determined plural positions of an audiometer switch to data output signals; comprising the steps of:
determining a first input signal corresponding to a first certain position of the switch;
storing said first input signal;
determining a second input signal corresponding to a second certain position of the switch;
comparing said first and second input signals to determine the possible difference between the first and second positions of the switch;
providing an output signal condition corresponding to said second position only when a certain predetermined relation is determined by said comparison;

said output signal condition being a first kind of signal condition comprising binary coded digit data printing information corresponding to said second position of the switch, and being provided only when said comparison determines that a certain first predetermined difference exists between said first and second positions of said switch; and
said output signal condition being a second kind of signal condition, in response to said comparison determining that a certain second predetermined difference exists, comprising binary coded digit data printing information corresponding to a plural number of data printing location spaces for each increment of said second predetermined difference determined by said comparison to exist between said first and second positions of said switch.

10. Method as in claim 9, further comprising the steps of:
determining an input signal corresponding to the setting of a second switch; and
at a time after said output signal condition occurs, providing a second switch output signal condition comprising binary coded digit information corresponding to said second switch setting input signal.

11. Method of converting manually determined plural positions of a switch to data output signals; comprising the steps of:
determining a first input signal corresponding to a first certain position of the switch;
storing said first input signal;
determining a second input signal corresponding to a second certain position of the switch;
comparing said first and second input signals to determine the possible difference between the first and second positions of the switch;
providing an output signal condition corresponding to said second position only when a certain predetermined difference between said first and second positions of the switch is determined by said comparison;
determining an independent input signal corresponding to the setting position of a second switch; and
after said output signal condition occurs, providing a second switch output signal condition in binary coded digit information corresponding to said independent input signal;
said independent input signal including a signal component having a first state in response to an odd-numbered certain digit of said setting position of said second switch, and having a second state in response to an even-numbered said certain digit; and
said second switch output signal corresponding only to a first predetermined indicium in response to said first state, and corresponding only to a second predetermined indicium in response to said second state.

12. Apparatus for providing data output signals indicating switch position settings of an audiometer, comprising:
a first register means selectively operative to receive a first input signal condition corresponding to the setting of a first switch of on audiometer;
a second register means selectively operative to receive a second input signal condition corresponding to the setting of a second switch of the audiometer;

third register means selectively operative to receive signal conditions stored in said second register means;

comparator means responsive to the signal conditions in said second register means and said third register means to provide output conditions corresponding to the relation between the signal conditions in said second and third register means;

control means responsive to a control input signal condition to cause said first and second register means to receive and store the respective first and second input signal conditions from the audiometer switches;

first bistable circuit means responsive to the output of said comparison means to assume a first state if said output corresponds to a certain first predetermined relation between the switch setting signal stored in said second register means and a previous switch setting signal stored in said third register means;

data circuit means operative to convert said first and second input signal conditions to an output condition for operating a data printing means;

circuit means operative in response to said first state of said bistable circuit means and a first data control signal from said control means to supply the second input signal condition stored in said second register means to said data circuit means;

circuit means operative in response to a data control signal from said control means subsequent to said first data control signal to supply the first input signal condition stored in said first register means to said data circuit means; and circuit means operative in response to a control signal from said control means subsequent to said first data control signal to store in said third register means the second input signal condition previously stored in said second register means and subsequently to clear said first and second register means.

13. Audiometric data conversion apparatus for converting audiometer switch position setting to printable output data, comprising:

first circuit means connected to receive a present input signal condition corresponding to a present position of a first selectively variable input switch means;

a first register means which is selectively operative to receive and retain an input signal condition previously retained in said first circuit means;

means connected to said first circuit means and operative after said first register means receives said present input signal condition to modifiy the present input signal condition in said first circuit means to correspond to a certain change in said present switch position of said first variable switch means;

comparison means responsive to said modified present input signal condition retained in said first circuit means and to said prior input signal condition in said first register means, said comparison means being operative to compare the modified present input signal condition in said first circuit means with the prior input signal condition previously supplied to said first register means, and to provide an output signal condition corresponding to the difference between the prior and the modified present input signal conditions; and third circuit means operative to receive said present input signal condition from said register means only in response to a predetermined output signal condition from said comparison means indicating that a certain difference exists between said present and prior positions of the first variable switch means.

14. Apparatus as in claim 13, wherein:

said output signal condition provided by said comparison means is a first predetermined signal condition corresponding to a first predetermined relation between present and prior positions of said first variable switch means;

said comparison means is operative to provide a second predetermined output signal condition corresponding to a second predetermined relation between said existing and prior variable switch positions; and comprising fourth circuit means operative in response to said second predetermined output signal from said comparison means to provide to said third circuit means a signal condition corresponding to the amount of switch position variation denoted by the difference between said modified present input signal condition and said prior input signal condition.

15. Audiometric data conversion apparatus as in claim 13, wherein:

said comparison means is initially operative to compare the present input signal condition with a prior input signal condition which is retained in said second register means and which corresponds to a prior position of said switch means, and to provide a first comparison signal condition indicating whether the present position of said switch is incrementally changed in a certain first mode, to provide a second comparison signal condition indicating that the present position has incrementally changed in a certain second mode, and to provide a third comparison signal condition indicating that the present position is unchanged relative to said prior position of said switch; and further comprising means responsive to said first comparison signal condition to generate a first print control signal which conditions a data printing means to receive and print audiometric information obtained at said first mode increment of change in the switch position;

means responsive to said second comparison signal condition to generate a second print control signal which conditions the data printing means to receive and print audometric information obtained at said second mode increment of change in the switch position; and means responsive to said third comparison signal condition to provide an error signal condition.

16. Apparatus as in claim 13, wherein said third circuit means is operative to covert said present input signal condition into signals suitable for operating data printing means.

17. Audiometric data conversion apparatus as in claim 13, wherein:

said first circuit means is operative to receive input signal conditions corresponding to the position of a frequency selector switch means;

said third circuit means is operative to convert said present signal condition into signals for conditioning a data printer to receive and print information corresponding to settings of said frequency selector switch means; and further comprising data register means operative to receive and store signals correspondig to the setting of an attenuator control means at each setting of said frequency selector means; and circuit means operative in response to conditioning of the data printer to feed said attenuator control setting signals from said data register means to the conditioned data printer.

* * * * *